United States Patent
Ross (10) Patent No.: US 8,784,365 B2
(45) Date of Patent: Jul. 22, 2014

(54) SYSTEM AND METHOD FOR CONTROLLING FLUID FLOW RATE AND MONITORING AND RECORDING FLUID PRESSURE DURING A MEDICAL INFUSION

(75) Inventor: Christopher D. Ross, Davie, FL (US)

(73) Assignee: Engineering Resources Group, Inc., Hialeah, FL (US)

( * ) Notice: Subject to any disclaimer, the term of this patent is extended or adjusted under 35 U.S.C. 154(b) by 618 days.

(21) Appl. No.: 12/561,209

(22) Filed: Sep. 16, 2009

(65) Prior Publication Data

US 2010/0100071 A1    Apr. 22, 2010

Related U.S. Application Data

(60) Provisional application No. 61/097,425, filed on Sep. 16, 2008.

(51) Int. Cl.
*A61M 31/00*    (2006.01)
(52) U.S. Cl.
USPC .............................................. 604/65
(58) Field of Classification Search
USPC ................................................ 604/65, 66, 67
See application file for complete search history.

(56) References Cited

U.S. PATENT DOCUMENTS

| | | | |
|---|---|---|---|
| 4,710,163 A * | 12/1987 | Butterfield | 604/65 |
| 6,183,433 B1 * | 2/2001 | Bays | 604/22 |
| 2006/0270971 A1 * | 11/2006 | Gelfand et al. | 604/66 |
| 2008/0097287 A1 * | 4/2008 | Nelson et al. | 604/65 |
| 2008/0146996 A1 * | 6/2008 | Smisson et al. | 604/67 |

* cited by examiner

*Primary Examiner* — Manuel Mendez
(74) *Attorney, Agent, or Firm* — The Concept Law Group, P.A.; Scott D. Smiley (57) ABSTRACT

A system for controlling an infusion of fluid into living tissue includes a catheter shaped to be introduced within living tissue and operable to deliver a fluid to a location within the living tissue, a fluid infusion pump mechanically coupled to the catheter and operable to pump fluid through the catheter and, thereby, into the location, the fluid infusion pump having at least two fluid pumping states, a fluid pressure monitor fluidically coupled to the catheter and operable to measure a pressure of the fluid within the catheter, and a processor communicatively coupled to the fluid infusion pump and the fluid pressure monitor, the processor operable to select between the at least two fluid pumping states based upon the measured pressure of the fluid within the catheter.

12 Claims, 13 Drawing Sheets

| A/D Channel ==> | CH 1 Pressure | CH 2 Pressure | CH 3 Pressure | CH 4 Pressure | CH 5 Pressure | CH 6 Pressure | CH 7 Cal Pressure | CH 8 |
|---|---|---|---|---|---|---|---|---|
| Raw Data | 10548.9 | 10584.9 | 8732.0 | 8734.4 | 8732.1 | 8733.2 | 8465.8 | 10440.8 |
| Voltage [V] | 2.877 | 2.921 | 0.659 | 0.662 | 0.659 | 0.661 | 0.334 | 2.745 |
| Pressure [mmHg] | 8.018 | 10.230 | -117.567 | -117.398 | -117.562 | -117.483 | -0.314 | |
| Cal. Offset [V] | 2.73639 | 2.74000 | 2.74000 | 2.74000 | 2.74000 | 2.74000 | 0.34165 | |
| Cal. Gain [mmHg/V] | 56.99571 | 56.50000 | 56.50000 | 56.50000 | 56.50000 | 56.50000 | 42.16380 | |
| Status | OK | OK | No 'DIN' | No 'DIN' | No 'DIN' | No 'DIN' | | |

Calibration Instructions

Calibration Pressure Sensor
1. Vent the Calibration Pressure Sensor to atmosphere.
2. Click the "CH7 Offset" button.
3. Apply "100mmHg of pressure to the Calibration Pressure Sensor.
4. Enter the measured value and click the "CH7 Gain" button.

Pressure Sensor
1. Select Pressure Sensor to calibrate (AD Channel):
2. Vent the Pressure Sensor to atmosphere.
3. Click the "CH Offset" button.
4. Connect the Calibration Pressure Sensor and Pressure Sensor together and apply "100mmHg of pressure.
5. Click the "CH Gain" button.

SYSTEM AND METHOD FOR CONTROLLING FLUID FLOW RATE AND MONITORING AND RECORDING FLUID PRESSURE DURING A MEDICAL INFUSION

FIELD OF THE INVENTION

The present invention relates generally to catheters, and more particularly relates to monitoring the pressure of fluid within a catheter during fluid delivery to a location within a human body and to preventing the pressure within the catheter from exceeding a predefined delivery pressure limit.

BACKGROUND OF THE INVENTION

Catheters are tubular passageways that, during a medical procedure, can be inserted into a body. Usually, the catheter is a thin, flexible tube; however, catheters can also be larger and usually more solid passageways. Catheters provide several functions, such as providing for delivery of fluids into the body, drainage of fluids out of the body, and more.

One use of catheters is to provide delivery of drugs to treatment areas of the brain. These catheters are inserted through the soft brain tissue and guided to the location where pharmaceuticals or other fluid treatments are to be delivered. One problem that occurs during catheter insertion is obstruction of the tip of the catheter fluid passageway. These obstructions are, in large part, due to the extremely soft consistency of living brain tissue, which readily separates and pushes into the open end of the catheter.

Medically-therapeutic fluid is delivered through the catheter and to the treatment site by manual compression of a syringe or delivery by a mechanical infusion pump. However, if the tip of the catheter is obstructed, fluid cannot flow to the delivery site. The effect is that a sharp increase in pressure builds up inside the catheter. If the pressure releases all at once, i.e., the obstruction and fluid forcefully and instantly exit the tip of the catheter, tissue will likely be decimated, potentially causing severe damage to the brain. Again, the procedures to the brain are particularly susceptible to this type of damage as neural tissue is soft and can easily be destroyed by a pressurized liquid force.

Additionally, if the fluid does not exit the catheter properly, instead of being delivered to the treatment site, the fluid is forced away from the treatment site, travels back out of the catheter entry path (between the exterior of the catheter and the brain tissue), and out of the brain. Alternatively, the fluid is blasted through the treatment site and is delivered to an unintended area within the body. This is highly undesirable, especially because neurological medicines are often delivered in very small doses and, therefore, are measured with extremely high precision. Any loss of fluid destroys the dosage calculation, as it is virtually impossible to determine the amount of medicine lost or the contents of a portion of a compound lost. Delivery of medicines to tissue not intended to be treated can have harmful effects on that tissue and, for that reason, must be avoided. In addition, neurological medicines are often very expensive and, for at least this reason, losses should be avoided.

Although catheters used for neurological treatments are more susceptible to obstructions than those used for treatment of other areas, clogging is still highly likely and can cause damage, can introduce uncertainty to treatment procedures, and can result in unnecessary financial waste.

Therefore, a need exists to overcome the problems with the prior art as discussed above.

SUMMARY OF THE INVENTION

The invention provides a system and method for controlling fluid flow and monitoring pressure during a medical infusion that overcomes the hereinafore-mentioned disadvantages of the heretofore-known devices and methods of this general type.

With the foregoing and other objects in view, there is provided, in accordance with the invention, a method for controlling an infusion of fluid into living tissue, where the method includes the steps of inserting a tubular catheter into living tissue, thereby creating a passageway for fluid introduction into the living tissue, initiating a fluid pumping process through the passageway, monitoring a pressure of the fluid within the passageway, and modifying the fluid pumping process in response to determining that the pressure exceeds a predefined limit.

In accordance with another feature, an embodiment of the present invention includes producing a visual representation of the pressure.

In accordance with a further feature of the present invention, the passageway includes a tubular hollow cannula.

In accordance with a further feature of the present invention, the fluid pumping process is performed either by pumping fluid into the passageway with an electrical, automatic, pumping device or pumping fluid into the passageway with a mechanical, hand-controlled, pumping device.

In accordance with yet one more feature of the present invention, the modifying step is performed by either halting the fluid pumping process, pulsing the fluid pumping process, or withdrawing the passageway a distance and reinitiating the fluid pumping process.

In accordance with another feature, an embodiment of the present invention also includes a system for controlling an infusion of fluid into living tissue, where the system includes a catheter shaped to be introduced within living tissue and operable to deliver a fluid to a location within the living tissue, a fluid infusion pump mechanically coupled to the catheter and operable to pump fluid through the catheter and, thereby, into the location, the fluid infusion pump having at least two fluid pumping states, a fluid pressure monitor fluidically coupled to the catheter and operable to measure a pressure of the fluid within the catheter, and a processor communicatively coupled to the fluid infusion pump and the fluid pressure monitor, the processor operable to select between the at least two fluid pumping states based upon the measured pressure of the fluid within the catheter.

In accordance with yet another embodiment of the present invention, the pressure data (numeric and chart) present instantaneous feedback to the surgeon on the quality of the infusion procedure. The shape of the pressure curve on the chart is highly indicative of the presence of an occlusion, reflux/backflow, leakage away from the therapeutic target and other characteristics of good and bad infusions. The pressure data provides an instant status of the procedure that allows the surgeon to adjust the treatment protocol for a favorable outcome where the surgeon would otherwise have no timely feedback.

Although the invention is illustrated and described herein as embodied in a novel and efficient system and method for controlling fluid pressure during a medical infusion procedure, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. The figures of the drawings are not drawn to scale.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

DETAILED DESCRIPTION

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the catheter.

The present invention provides a novel and efficient system and method for controlling fluid pressure during a medical infusion procedure. Embodiments of the invention provide a catheter, a fluid infusion pump, a fluid pressure transducer, and a processor that, together, prevent the infusion pump from operation when excessive fluid pressure accumulation is detected during a delivery procedure.

Figure 1:
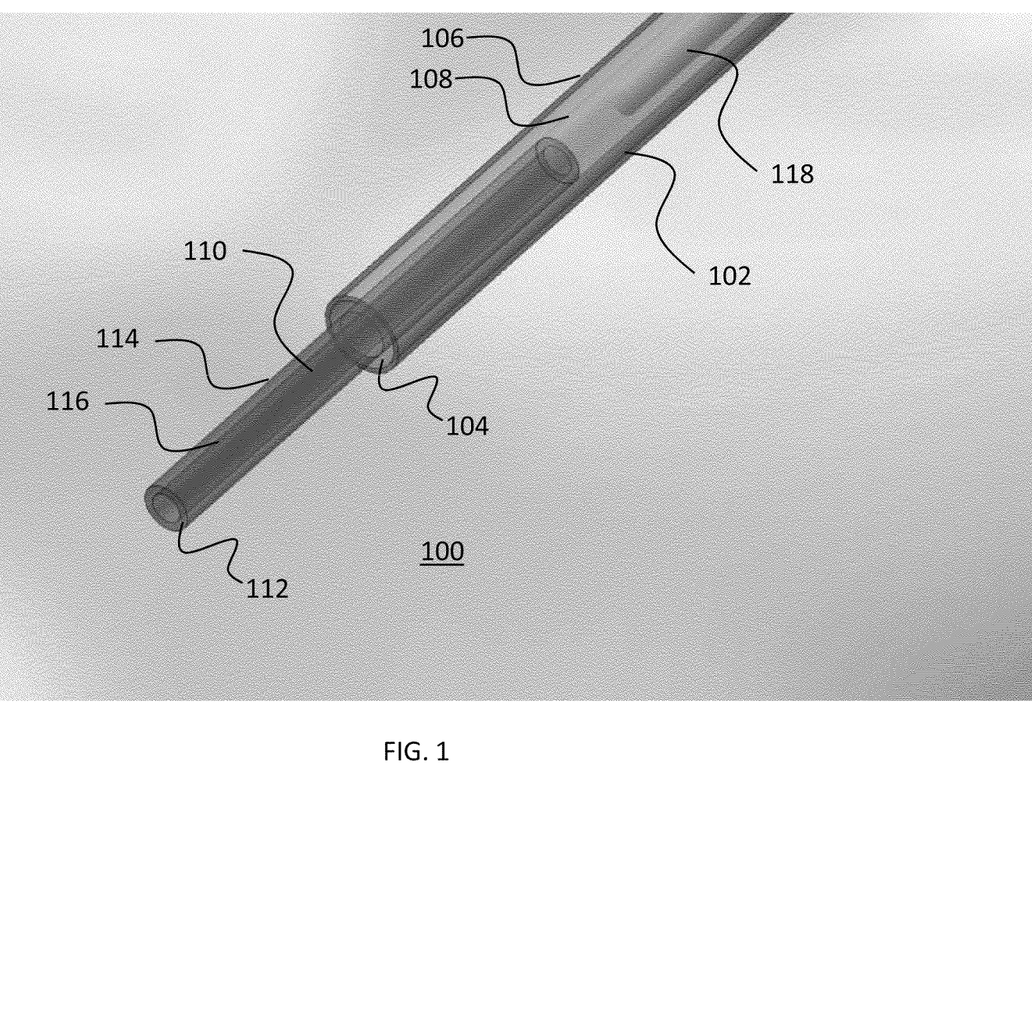
FIG. 1 is a fragmentary, transparent, perspective view of an exemplary embodiment of a catheter device in accordance with the present invention.

Referring now to FIG. 1, a catheter 100 includes a cannula 102. The cannula 102 is a tubular passageway with an exterior surface 106 and an interior surface 108. Inserted within the distal end 104 and fixedly coupled to the interior surface 108 of the cannula 102 is a tip 110. The tip 110 has an exterior surface 114 and an interior surface 116.

Also shown in the transparent view of FIG. 1, a stylet 118 is positioned within the cannula 102. The stylet 118 provides a stiffness to the catheter as it is inserted into and through tissue. The illustrated location of the stylet 118 within the cannula 102 provides a fluid path 200, shown by dashed lines in FIG. 2. The fluid path 200 starts from the gap between interior surface 108 of the cannula 102 and the outer surface 120 of the stylet 118, continues through the interior 116 of the tip 110, and exits out into the treatment area 202.

Figure 2:
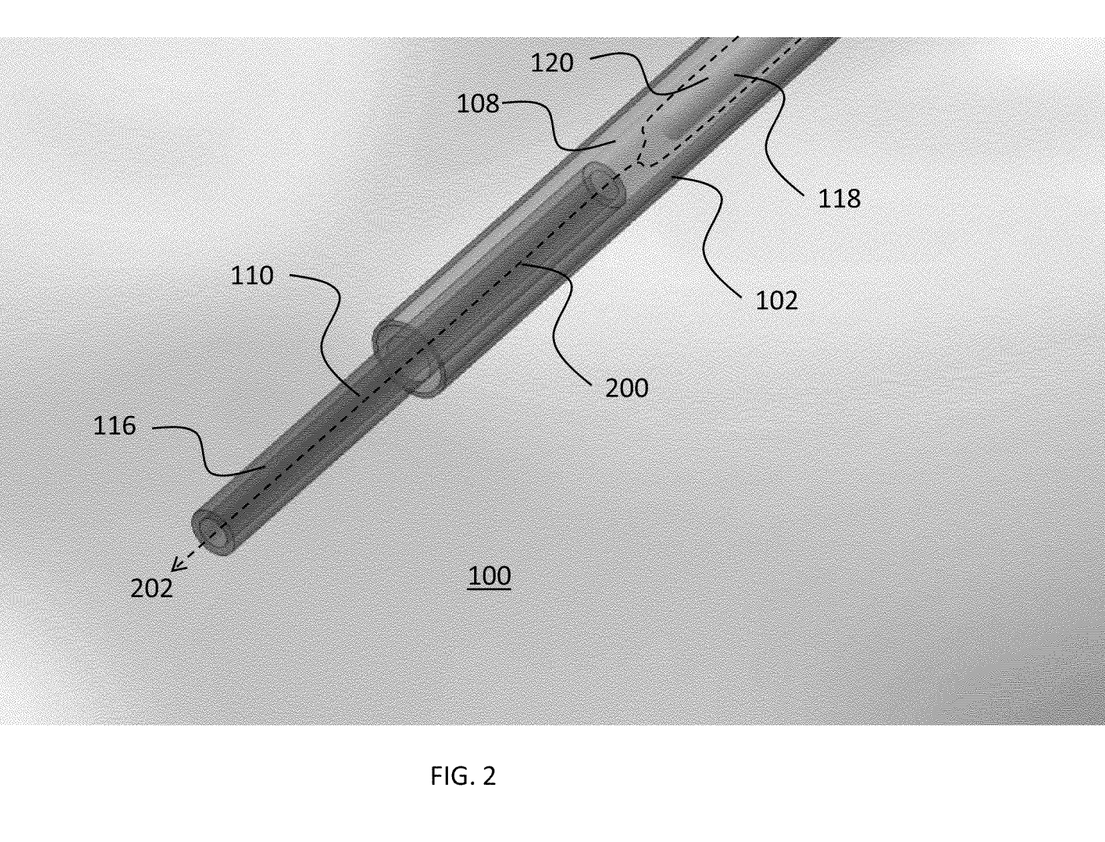
FIG. 2 is a fragmentary, transparent, perspective view of the catheter device of FIG. 1 showing a fluid path through the catheter.
Figure 3:
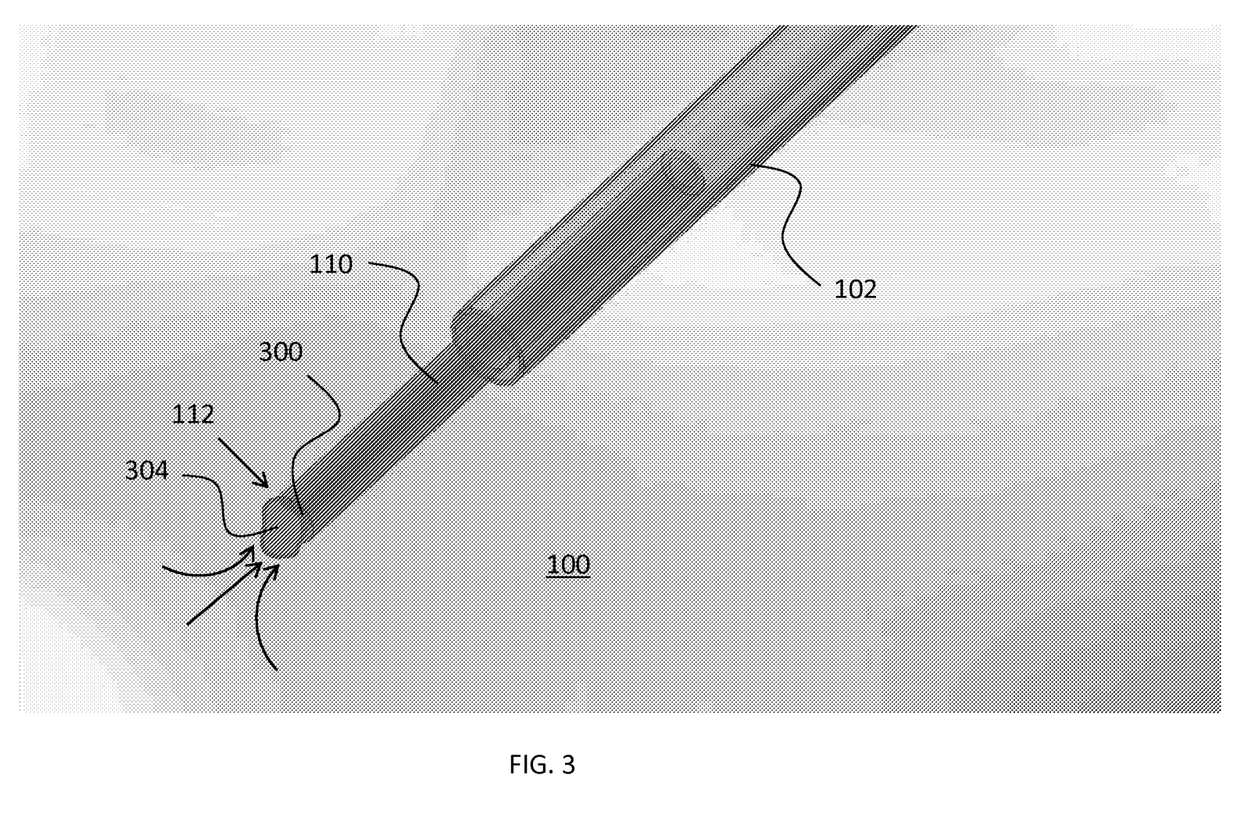
FIG. 3 is a fragmentary, transparent, perspective view of the catheter device of FIG. 1 showing biological material blocking the catheter fluid exit point.

With the stylet's orientation within the cannula 102, as shown in FIGS. 1-3, during movement of the catheter 100 through tissue, the opening 300 (see FIG. 3) in the distal end 112 of the tip 110 is susceptible of being filled with biological material 304. This susceptibility is due to the fact that the passageway through the tip 110 is empty and provides a canal leading right into the cannula 102, i.e., the reverse of the fluid flow 200 shown in FIG. 2. When material 304 is present within the tip 110, the fluid path 200 is interrupted and fluid is unable to flow and, as a result, fluid is not delivered to the treatment site.

Figure 4:
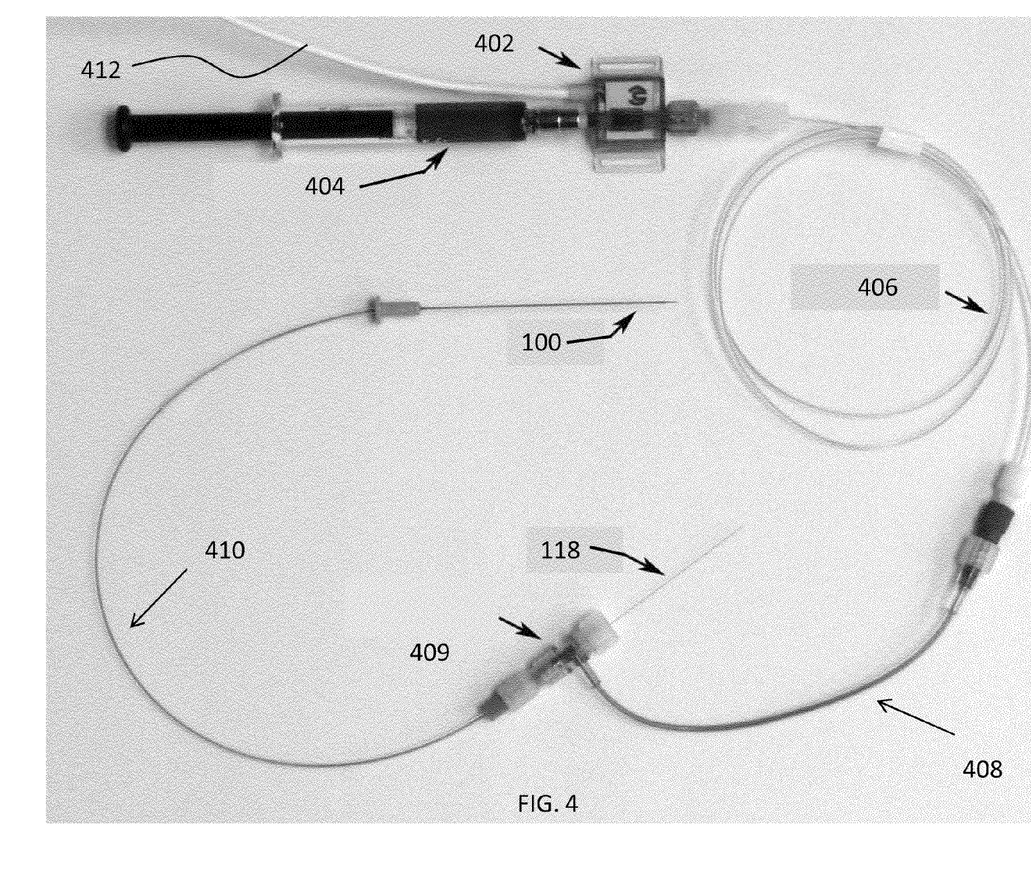
FIG. 4 is a photograph from above a portion of an inventive manual infusion pump system for controlling an infusion of fluid into living tissue in accordance with the present invention.

FIG. 4 shows a fluid delivery and pressure measuring portion of an inventive system for controlling an infusion of fluid into living tissue in accordance with the present invention. The fluid delivery and pressure measuring portion shown in FIG. 4 includes a fluid passageway having a proximal infusion tubing 406 connected through a luer connector to a lateral infusion shunt 408, which projects laterally out from a Touhy-Borst valve 409. Both the fluid and the stylet 118 are able to pass through delivery tubing 410, which terminates at the catheter 100, the catheter portion 100 being shaped to be introduced within living tissue. The fluid passageway 406, 408, 409, 410, 100 is operable to precisely deliver a medically therapeutic fluid to a location within the living tissue in which it is inserted. The exemplary assembly shown in FIG. 4 is configured to precisely deliver a medically therapeutic fluid into a human brain, for example.

A fluid infusion pump (syringe) 404 is mechanically coupled to the fluid passageway 406, 408, 409, 410, 100 and is operable to pump fluid into the fluid passageway 406, 408, 409, 410, 100. In the particular embodiment shown, the fluid infusion pump 404 is a standard syringe and the pumping is performed purely mechanical by an operator's hand.

Figure 5:
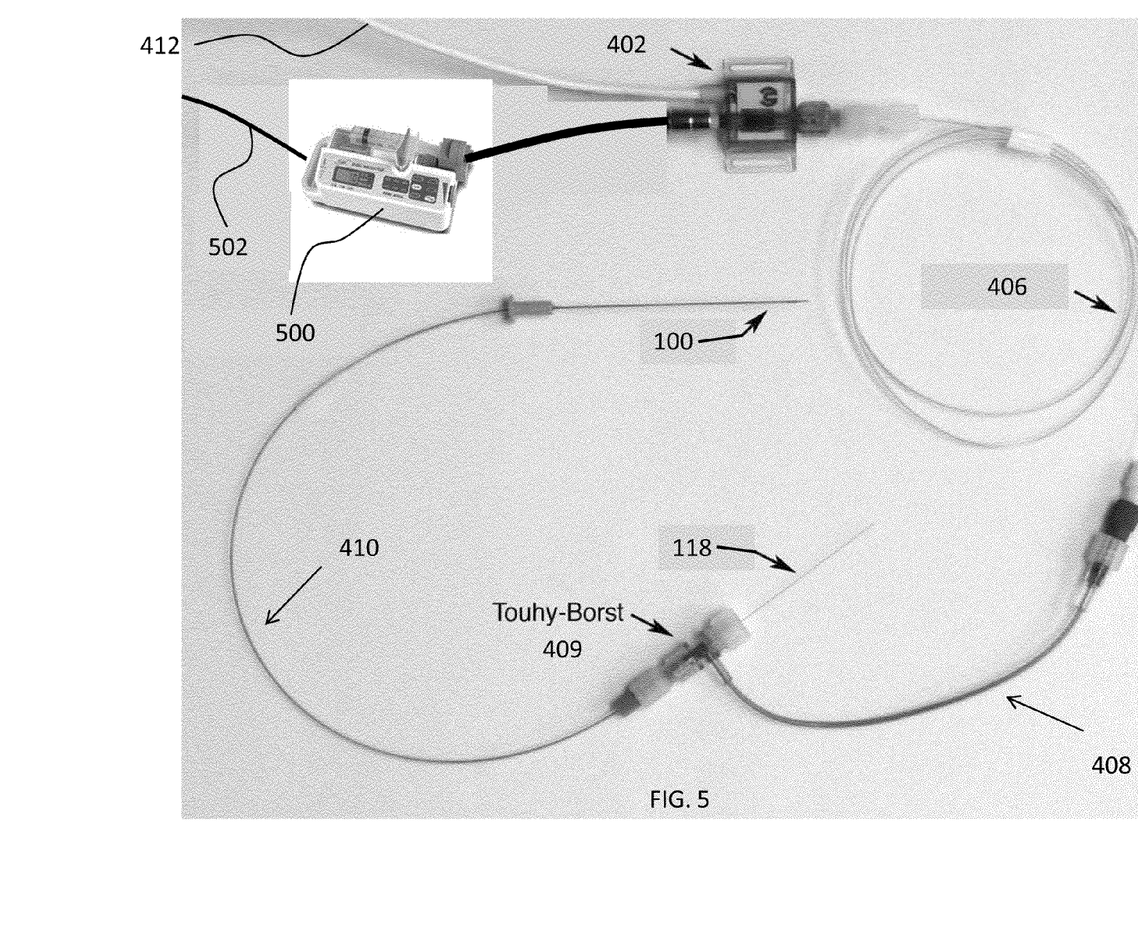
FIG. 5 is a photograph from above a portion of an inventive automatic infusion pump system for controlling an infusion of fluid into living tissue in accordance with the present invention.

Alternatively, FIG. 5 depicts an electronically-controlled automated infusion pump 500, i.e., one that does not require an operator's hand control. Both automated and hand-controlled fluid infusion pumps are well-known in the art. The automated infusion pump 500 includes a control signal path 502 that transports signals from a non-illustrated control unit for controlling the fluid output and possibly other functions of the automated infusion pump 500.

Also shown in FIGS. 4 and 5 is a fluid pressure sensor 402 that is mechanically and fluidically coupled to the fluid passageway 406, 408, 409, 410, 100. The fluid pressure sensor 402 is operable to measure a pressure of the fluid within the fluid passageway 406, 408, 409, 410, 100 and, in the embodiments shown in FIGS. 4 and 5, is a mechanical pressure transducer that is able to convert a detected fluid pressure to an output voltage. Any device or method of measuring the pressure of a fluid can be used and it should be noted that the position of the fluid pressure sensor 402 shown in FIGS. 4 and 5 is merely exemplary. The present invention is in no way limited to the fluid pressure sensor 402 being at an output of the automated infusion pump 500.

Figure 6:
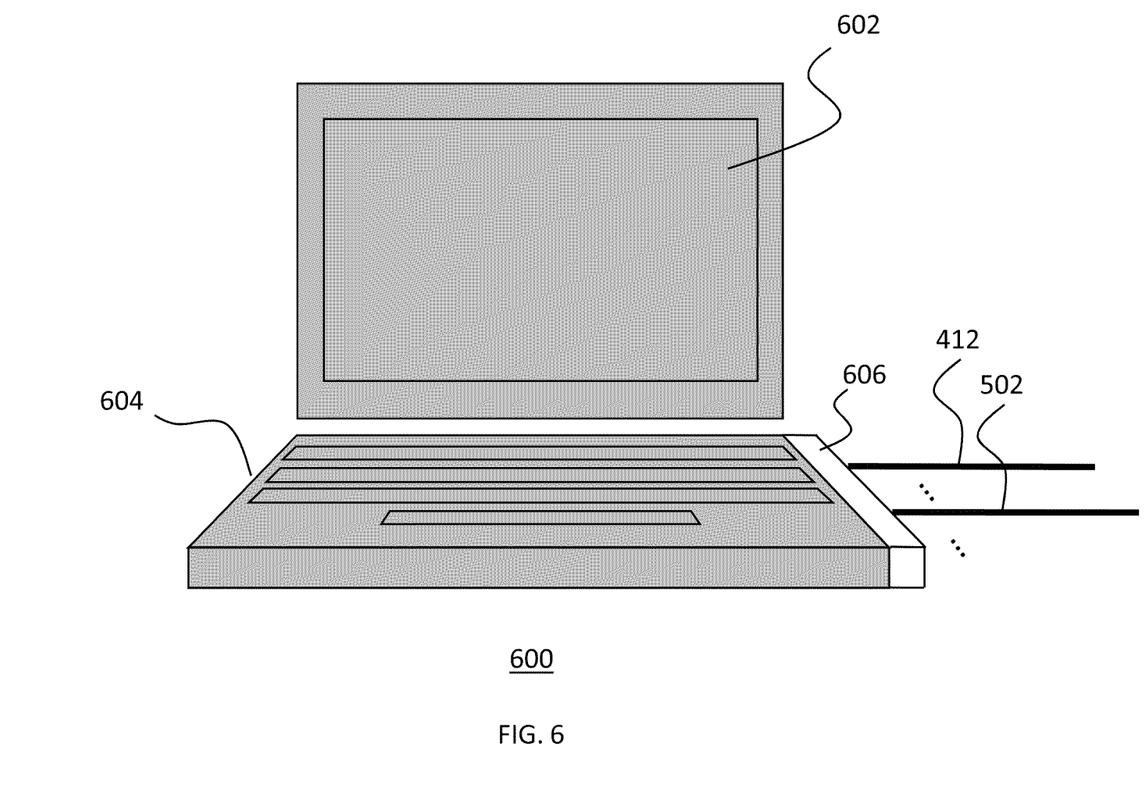
FIG. 6 is perspective view of a diagrammatic computing and display system in accordance with the present invention.

The fluid pressure sensor 402 is communicatively coupled through communications path 412 to an interface 606 of a computing and display system 600, which can be integral with the sensor 402 and/or the path 412. The computing and display system 600 is shown in FIG. 6 as a traditional laptop computing system with a display 602, a user interface 604, and the interface 606 communicatively coupled to the laptop. The system may have form factors ranging from the Laptop system 600 to Patient Monitor style systems to Handheld PC/Smart Phone style systems. The interface 606 couples one or more communications paths 412 and one or more control lines 502 to the computing and display system 600. The user interface 604 is, in this embodiment, is a keyboard for receiving user input.

The display 602, through numeric indicators, graphical indicators, or both, indicates the pressure within the fluid passageway 406, 408, 409, 410, 100, along with infusion volume infused, operating status of each infusion pump 500 and pressure sensor 402. In particular, a processing system 700, shown in FIG. 7, causes the display 602 to indicate to an operator of the fluid infusion pump 404 the measured pressure and when a specific pressure limit is being approached, has been met, or has been exceeded. In response, the operator of the fluid infusion pump 404 can adjust the infusion flow rate to compensate for the pressure profile being indicated on the display 602. Alternatively, where the infusion pump 500 is electronically controlled, i.e., the embodiment shown in FIG. 5, the computing and display system 600 can respond to a detected excessive fluid pressure by modifying an operation of the infusion pump 500 through control line 502 attached to the interface 606. The modifying can be, for instance, halting the pumping operation, sending a short fast pulse of pressure along the fluid passageway 406, 408, 409, 410, 100 as an attempt to dislodge the obstruction in the line, or other modes.

Figure 7:
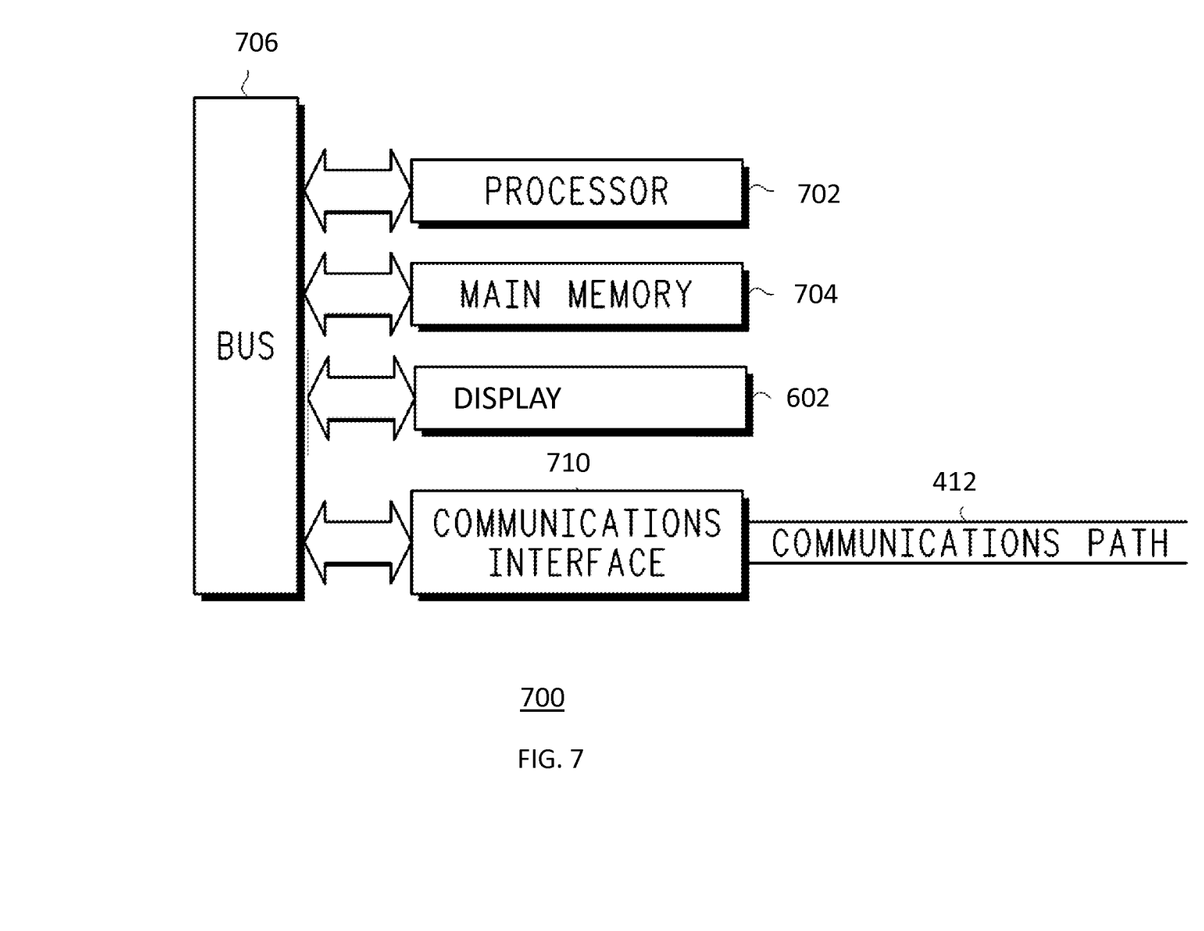
FIG. 7 is a high level block circuit diagram illustrating an exemplary embodiment of a computing system in accordance with the present invention.

FIG. 7 is a high-level block circuit diagram illustrating a detailed view of a processing system 700 useful for implementing the computing and display system 600. The processing system 700 is based upon a suitably configured processing system adapted to implement an exemplary embodiment of the present invention capable of interpreting and displaying the fluid pressure within the fluid passageway 406, 408, 409, 410, 100 and for controlling at least one automated fluid infusion pump 500.

In one exemplary embodiment of the present invention, the fluid pressure sensor 402 includes or is communicatively coupled with one or more processors, such as processor 702. The processor 702 is connected to a communication infrastructure 706 (e.g., a communications bus). Various software embodiments can replace or work in conjunction with this exemplary computer system. After reading this description, it will become apparent to a person of ordinary skill in the relevant art(s) how to implement the invention using other computer systems and/or computer architectures.

The processing system 700 also includes a memory 704, preferably random access memory (RAM), and may also include various caches and auxiliary memory as are normally found in computer systems. The memory 704 is useful for, for example, storing values for use in calibration functions and storing fluid-pressure limit values.

The processing system 700, in this example, includes a communications interface 710 that acts as an input and output and allows software and data to be transferred. Software and data transferred via communications interface 710 are in the form of signals which may be, for example, electronic, electromagnetic, optical, or other signals capable of being received by communications interface 710. The signals are provided to communications interface 710 through the communications path 412 coupled to fluid pressure sensor 402. The communications path 412 carries signals and may be implemented using wire or cable, fiber optics, a phone line, a cellular phone link, an RF link, and/or any other communication channel.

Computer programs (also called computer control logic) are stored in memory 704. Computer programs may also be received via communications interface 710. Such computer programs, when executed, enable the computer system 600 to perform the features of the present invention as discussed herein. In particular, the computer programs, when executed, enable the processor 702 to control and display fluid pressure during a medical infusion procedure.

Figure 8:
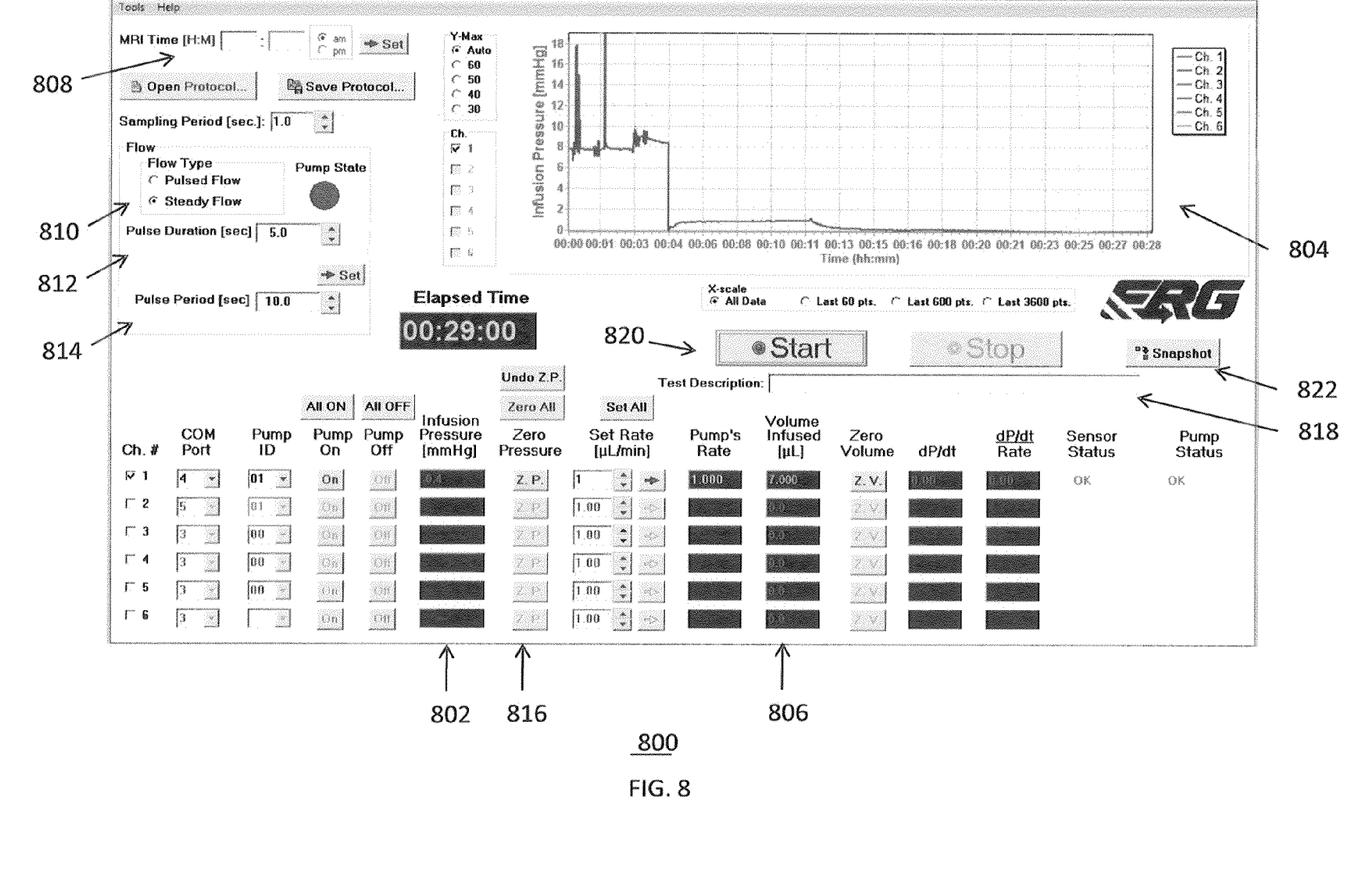
FIG. 8 is a pictorial representation of an exemplary computer-generated graphical user interface for a multi-channel pressure monitoring device according to an embodiment of the present invention.

FIG. 8 shows an exemplary computer-generated graphical user interface (GUI) 800 of a multi-channel pressure monitoring device showing exemplary data that can be determined by the computing and display system 600 and be shown on display 602. As can be seen in the GUI 800, multiple channels (1-6) can be monitored at a single time. Through any of these channels, the present invention is able to receive pressure readings from an infusion process pressure transducer 402, record the readings, and display the pressure values and other data in numeric form 802 and/or chart form 804 on the display 602. The computing and display system 600 can calculate or retrieve infusion volume data from the infusion pump 500 for display 806 that is infused during an infusion run, which is based on the pumping rate. The calculated infused volume 806 can be displayed in numeric form and chart form. Also shown in the GUI 800 is an infusion run elapsed time 808.

As shown in box 810, flow of automated infusion pump 500 can be controlled in at least two modes. Mode 1 is a steady fluid flow mode. In this mode the infusion pump 500 is started at the beginning of a run and stopped at the end of the run. As long at the fluid pressure does not exceed a preselected maximum value, the steady fluid mode does not need to be interrupted. However, if a fluid pressure exceeds a particular value, this mode may need to be halted. The second mode is a pulsed fluid flow mode and may be invoked, for example, when a clog in the fluid line causes the pressure to build. In this mode, the infusion pump 500 cycles on and off according to the time defined by the user in field 812 and the cycle period time defined by the user in field 814 until the end of the run.

Figure 9:
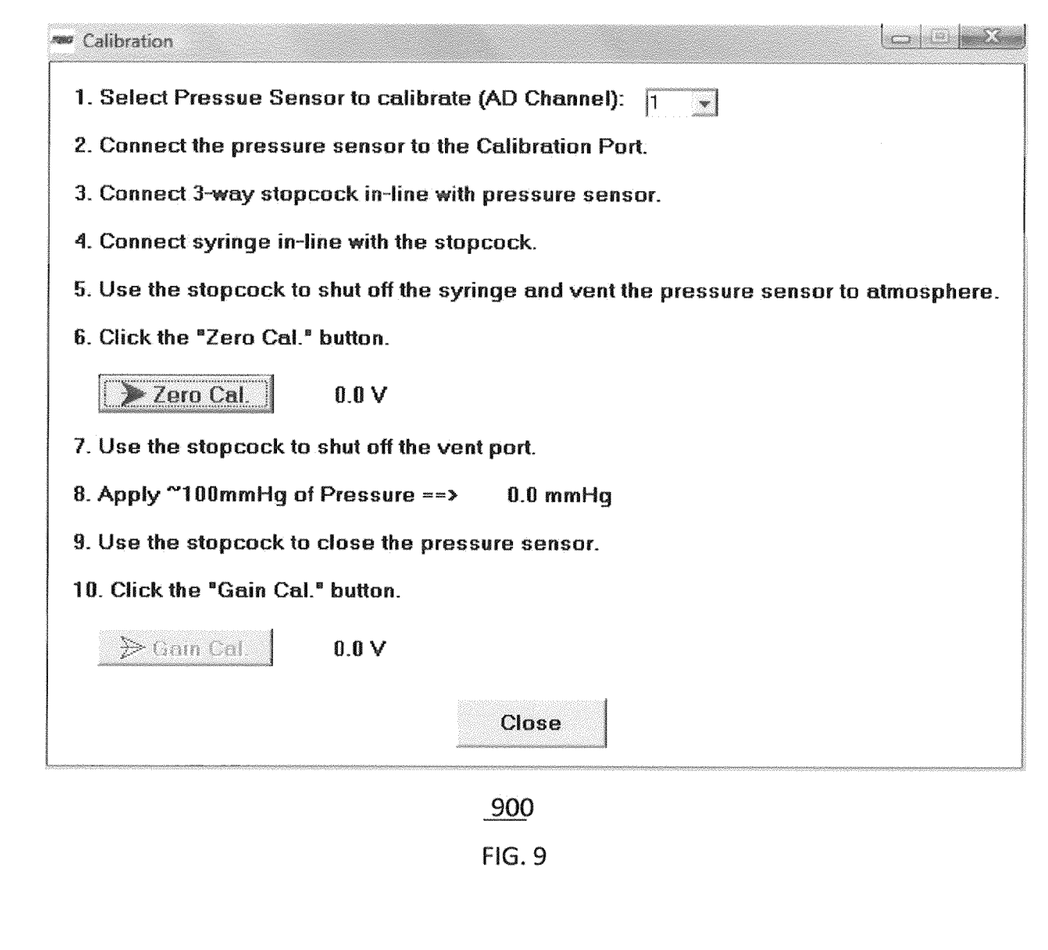
FIG. 9 is a computer-generated pictorial representation of a calibration screen for a multi-channel pressure monitoring device according to an exemplary embodiment of the present invention.

Embodiments of the present invention allow the pressure transducer 402 to be zeroed at any time by clicking a zero button 816. "Zeroing," as used herein, with respect to pressure transducer 402, means to offset the pressure reading so that the pressure data recorded/displayed represents gauge pressure at the tip of the catheter. Through a drop-down menu, such as the exemplary menu 900 of FIG. 9, a selected transducer can be calibrated against the internal reference pressure transducer 402. This is only necessary when a pressure transducer 402 is used in one of the input channel for the first time. As shown in FIG. 9, the menu 900 allows a user to select a particular pressure sensor if more than one sensor is attached to the interface 606. Once the sensor is selected, the user follows the instructions steps to perform the calibration. The steps shown in FIG. 9 are merely exemplary and fewer or more steps can be included in the calibration process.

Figure 10:
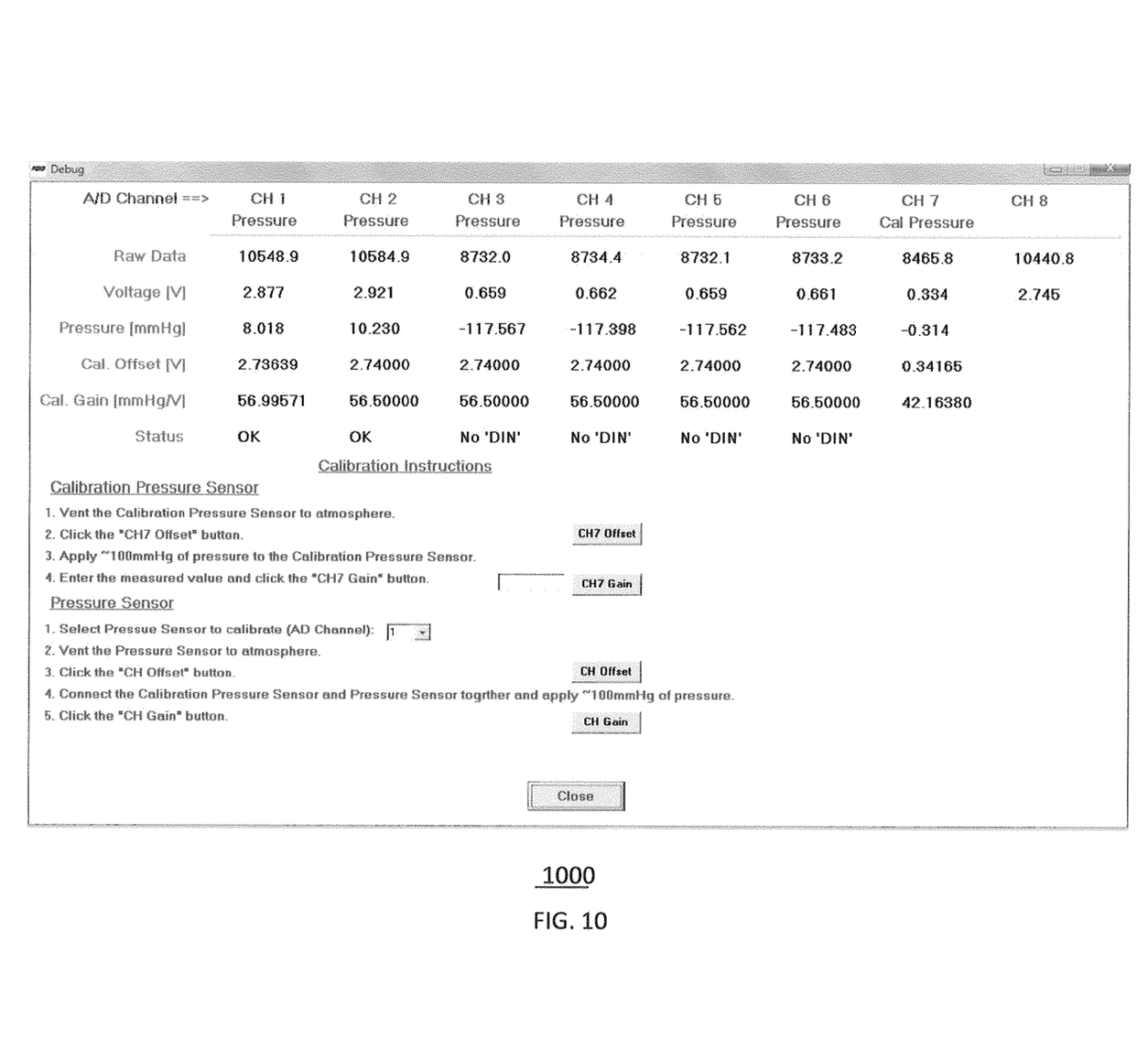
FIG. 10 is a computer-generated pictorial representation of a calibration screen for a multi-channel pressure monitoring device according to an exemplary embodiment of the present invention.

Through a password protected menu, such as exemplary menu 1000 shown in FIG. 10, a selected internal reference transducer can be calibrated against a National Institute of Standards & Technology (NIST) traceable, i.e., the calibration was performed by a company registered with NIST, to avoid unintended adjustment to calibration settings. The internal reference pressure transducer is used to calibrate the pressure transducer 402 on initial setup and on replacement.

Through menu 1000, the sampling rate of data recording is set through a user-selected input prior to initiating infusion pressure monitoring. The chart window 804 may be accessed at any time during a run to, for example, auto-scale the pressure data being charted or to fix the range of the values to be displayed. In addition, the chart window 804 may be configured at any time during a run to, for example, auto-scale the elapsed time data charted or to scroll a fixed number of time data points. In one embodiment, data identifying the volume of infused fluid is charted in window 804.

The description of the test can be entered in the description box 818 prior to initiation of the monitoring. In an exemplary embodiment of the present invention, data recording is initiated by clicking the START button 820 and either accepting the default file name or entering a file name in a dialog box and clicking "save." Once recording begins, the data being recorded and calculated is written to a file having either the default name or the user-specified name in a desired format, such as an ASCII file. The recording is stored in, for instance, memory 704. In one embodiment, the file header includes, but is not required to include or limited to:

a) Software revision;
b) Used input test description;
c) Time and date of the start of the test;
d) The data sampling time; and
e) The infusion pump run mode.

As an additional feature, a graphic image of the GUI 800, with all current data, can be recorded by clicking on the "Snap Shot" button 822 at any time. This graphic file can be named and stored in memory 704 with the date and time of the snap shot.

Figure 11:
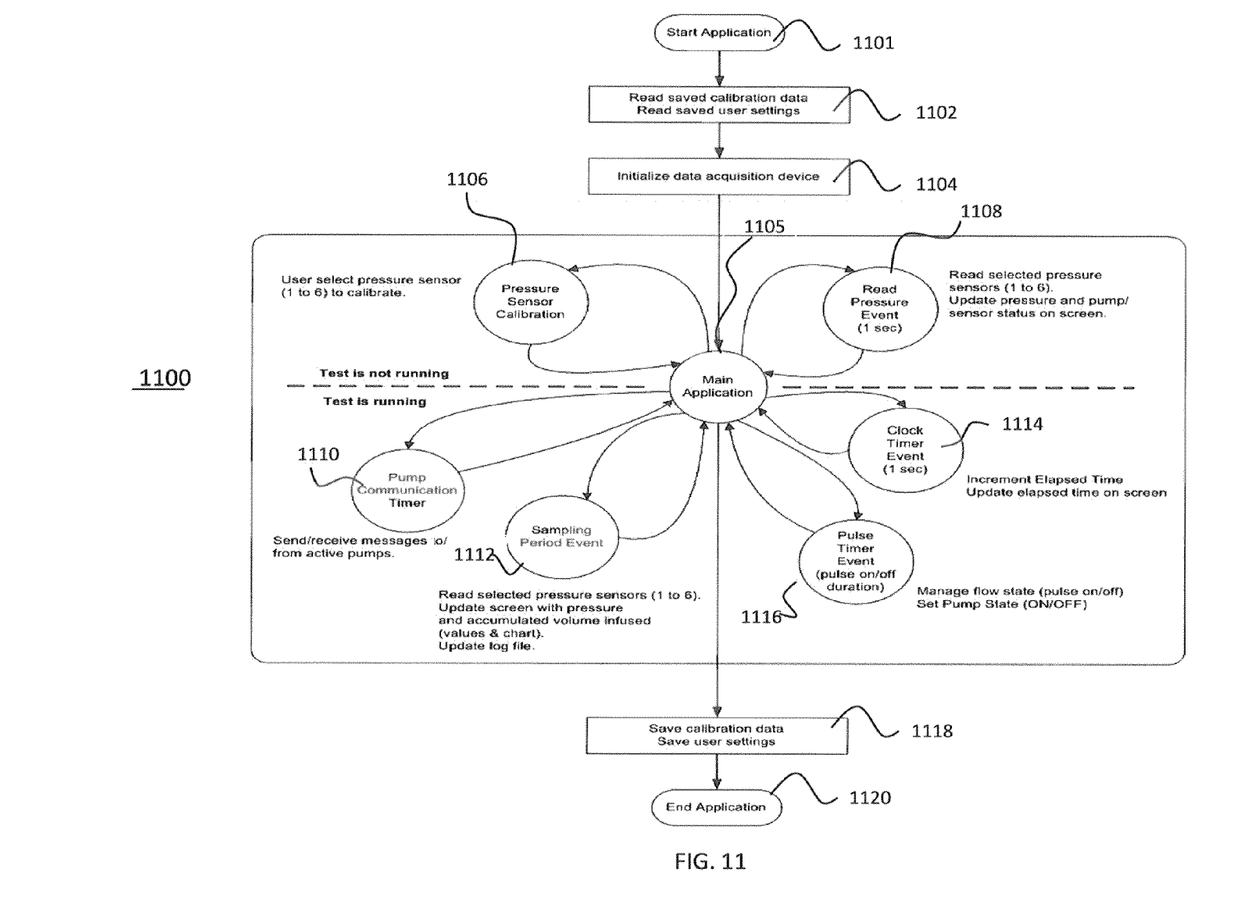
FIG. 11 is a process flow diagram illustrating a method of monitoring an infusion in accordance with an exemplary embodiment of the present invention.

FIG. 11 shows a process flow diagram of the present invention. The process 1100 starts at step 1101 and moves directly to step 1102 where saved calibration data and saved user settings are read from memory 704. Next, in step 1104, the data acquisition device is initialized. The data acquisition device can be andy internal circuitry that excites and reads the output voltage from the pressure transducer. This initialization includes utilizing the calibration data and user settings within subroutines carried out by the computer system 600.

The flow then proceeds, in step 1105, to the main application, represented in the GUI 800 shown in FIG. 8. From the main application, the user can select any one of several steps. Two possible steps can occur before the test begins. These steps include calibrating the pressure sensor, step 1106, or reading selected pressure sensors, step 1108, which also updates the pressure sensors and pump status readings on the GUI 800. Both steps 1106 and 1108 can be performed, only one of the steps can be performed, or neither can be performed, depending on many factors, such as, for example, the elapsed time since the previous monitoring session, whether new devices have been attached, changes in the environment, and others.

Once infusion monitoring begins, at least four additional steps/processes are possible and can be performed simultaneously. These steps include:

sending and/or receiving messages to and/or from active infusion pumps (step 1110);
reading selected pressure sensors (step 1112), which step can also include the process of updating the GUI 800 with pressure and accumulated volume of fluid infused;
incrementing the amount of elapsed time since the pumping process began (step 1114); and
managing a flow state (step 1116), i.e., steady pumping state, pulsed pumping state.

Once the recording operation 1105 finishes, the process moves to step 1118, where the calibration data and any user settings entered are saved in the memory 704. Finally, the process ends at step 1120.

Figure 12A:
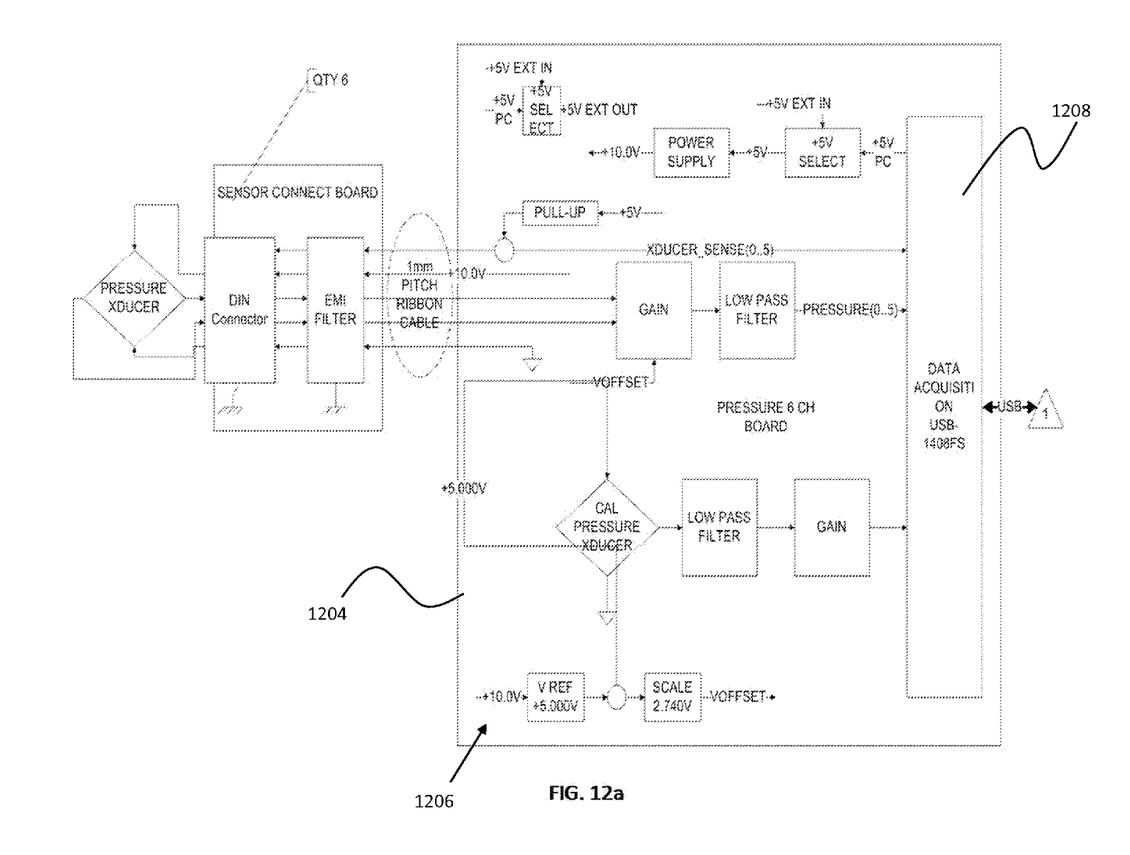
FIG. 12a is a partial schematic diagram of a system for measuring fluid pressure during an infusion and responding to detected pressure levels in accordance with an exemplary embodiment of the present invention.
Figure 12B:
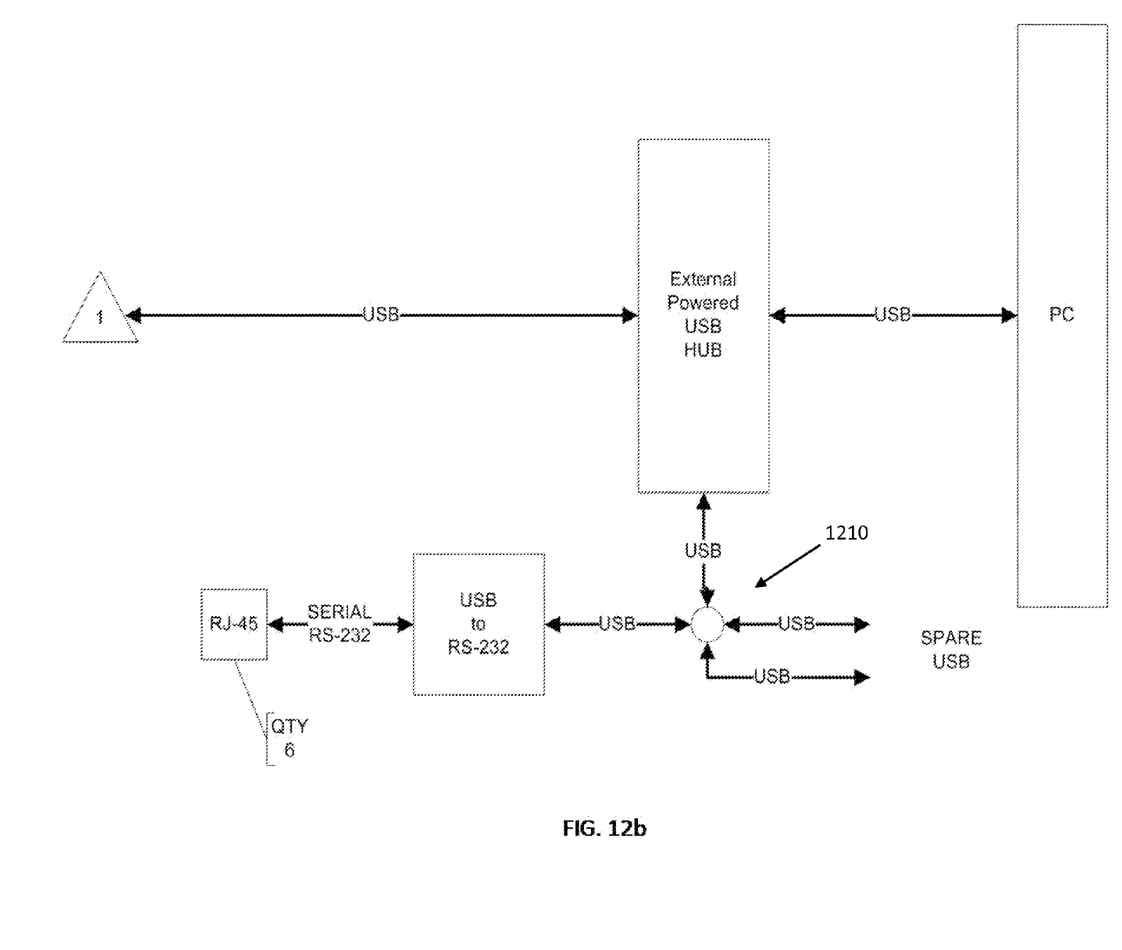
FIG. 12b is a continuation of the partial schematic diagram of FIG. 12a in accordance with an exemplary embodiment of the present invention.

FIGS. 12*a* and 12*b* show a more detailed schematic of one embodiment of the present invention. The main board 1204 houses the circuitry 1206 for communication with the Processor 702. The circuitry 1206 provides amplification and noise filtering for each pressure transducer channel. In addition the circuitry 1206 multiplexes the data from each channel through the data acquisition module 1208 on instructions from the Processor 702. All peripherals are linked to the processor 702 through universal serial bus ports 1210.

As should now be clear, embodiments of the present invention provide an advantage over prior-art devices by providing an infusion monitoring device and method of monitoring an infusion that identifies unwanted increases in fluid pressure during an infusion procedure and either alerts an operator of the unwanted pressure level or automatically alters a fluid infusion pump's pumping process.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A system for controlling an infusion of fluid into brain tissue, the system comprising:
    a tubular fluid passageway including a neural catheter portion shaped to be introduced within brain tissue and operable to deliver a fluid to a location within the living brain tissue;
    a fluid infusion pump mechanically and fluidically coupled to the fluid passageway and operable to pump fluid through the neural catheter portion into the location, the fluid infusion pump having at least two fluid pumping states;
    a fluid pressure sensor physically independent of the fluid infusion pump and mechanically and fluidically coupled to the fluid passageway and operable to measure a pressure of the fluid within the fluid passageway, the fluid pressure sensor operably configured to measure a pressure drop of approximately 100 millimeters of mercury (2 psi) or less across a portion of the fluid passageway;
    a processor communicatively coupled to the fluid infusion pump and the fluid pressure sensor, the processor operable to select between the at least two fluid pumping states based upon the measured pressure of the fluid within the fluid passageway; and
    a display coupled to the processor and operable to indicate a numerical value of the measured pressure of the fluid and to display a graphical representation of the pressure of the fluid as measured over a period of time.

2. The system according to claim 1, wherein the fluid infusion pump comprises an electrical, automatic, pumping device.

3. The system according to claim 1, wherein:
    the fluid pressure sensor is a pressure transducer.

4. The system according to claim 1, wherein the at least two fluid pumping states includes:
    halting a fluid pumping process; and
    pulsing a fluid pumping process.

5. The system according to claim 1, wherein the fluid comprises:
    a medically-therapeutic substance.

6. The system according to claim 1, wherein:
    the display is operable to indicate a pressure profile of the pressure within the fluid passageway.

7. The system according to claim 1, wherein the tubular fluid passageway comprises:
    a proximal infusion tube portion coupled to the fluid pressure sensor; and
    a delivery tube portion coupled between the proximal infusion tube portion and the catheter portion.

8. The system according to claim 1, wherein the fluid pressure sensor is operable to connect to an electrical, automatic pumping.

9. The system according to claim 1, wherein the at least two fluid pumping states include:
    a steady fluid flow mode; and
    a pulsed fluid flow mode, wherein the fluid infusion pump cycles on and off according to a predetermined time stored and communicated by the processor.

10. A system for controlling an infusion of fluid into brain tissue, the system comprising:
    a tubular fluid passageway including a neural catheter portion shaped to be introduced within brain tissue and operable to deliver a fluid to a location within the brain tissue, the tubular fluid passageway encapsulating a stylet operable translate within the tubular passageway to seal off a stepped tip to prevent an occlusion of tissue in the catheter during a catheter insertion;
    a fluid infusion pump mechanically and fluidically coupled to the fluid passageway and operable to pump fluid through the neural catheter portion into the location, the fluid infusion pump having at least two fluid pumping states and including:
    an electrical, automatic, pumping device;
    a fluid pressure sensor mechanically and fluidically coupled to the fluid passageway and operable to:
    measure a pressure of the fluid within the fluid passageway; and
    connect to the electrical, automatic pumping device; and
    a processor communicatively coupled to the fluid infusion pump and the fluid pressure sensor, the processor operable to select between the at least two fluid pumping states based upon the measured pressure of the fluid within the fluid passageway; and
    a display coupled to the processor and operable to indicate a numerical value of the measured pressure of the fluid and to display a graphical representation of the pressure of the fluid as measured over a period of time.

11. The system according to claim 10, wherein the at least two fluid pumping states include:
    a steady fluid flow mode; and
    a pulsed fluid flow mode, wherein the fluid infusion pump cycles on and off according to a predetermined time stored and communicated by the processor.

12. The system according to claim 10, wherein the tubular fluid passageway comprises:
    a proximal infusion tube portion coupled to the fluid pressure sensor; and
    a delivery tube portion coupled between the proximal infusion tube portion and the catheter portion.

* * * * *